(12) United States Patent
Roche et al.

(10) Patent No.: US 7,800,012 B2
(45) Date of Patent: Sep. 21, 2010

(54) ELECTRON GUN WITH A FOCUSING ANODE, FORMING A WINDOW FOR SAID GUN AND APPLICATION THEREOF TO IRRADIATION AND STERILIZATION

(75) Inventors: Michel Roche, Dijon (FR); Philippe Fontcuberta, Vendome (FR)

(73) Assignees: La Calhene, Vendome Cedex (FR); Physique & Industrie, Marsannay la Cote (FR)

( * ) Notice: Subject to any disclaimer, the term of this patent is extended or adjusted under 35 U.S.C. 154(b) by 1189 days.

(21) Appl. No.: 10/576,034

(22) PCT Filed: Oct. 19, 2004

(86) PCT No.: PCT/FR2004/002669

§ 371 (c)(1),
(2), (4) Date: Apr. 14, 2006

(87) PCT Pub. No.: WO2005/041241

PCT Pub. Date: May 6, 2005

(65) Prior Publication Data

US 2007/0145304 A1    Jun. 28, 2007

(30) Foreign Application Priority Data

Oct. 20, 2003    (FR) .................................. 03 50704

(51) Int. Cl.
*B23K 15/00* (2006.01)
*B23K 15/10* (2006.01)
*H01J 37/063* (2006.01)
(52) U.S. Cl. ............................. 219/121.27; 219/121.24

(58) Field of Classification Search .............. 250/492.3, 250/493.1; 219/121.12, 121.21, 121.24, 219/121.27; 313/446, 448, 454, 420
See application file for complete search history.

(56) References Cited

U.S. PATENT DOCUMENTS 2,602,751 A * 7/1952 Robinson .................. 250/492.3

(Continued)

FOREIGN PATENT DOCUMENTS

CA          1118180          2/1982

(Continued)

OTHER PUBLICATIONS

Bull et al. "An Electrostatic Electron Gun for Electron Beam Welding", Dec. 1970, pp. 97-104.*

*Primary Examiner*—Geoffrey S Evans
(74) *Attorney, Agent, or Firm*—Pearne & Gordon LLP

(57) ABSTRACT

An electron gun includes a sealed chamber under vacuum. A cathode having an emitting face is placed inside the chamber. An anode forms a sealed window, formed facing the emitting face in one of the walls of the chamber. The anode is capable of allowing electrons emitted by the emitting face to pass through. A biasing apparatus sets up a voltage between the anode and the cathode, capable of accelerating these electrons towards the anode, the electrons thus accelerated forming a beam that passes through the anode. The anode and the emitting face each have a curvature, the curvature of the anode making it capable of resisting a pressure difference between the inside and the outside of the chamber and being designed to cooperate with the curvature of the emitting face to focus the electron beam outside the chamber.

13 Claims, 5 Drawing Sheets

U.S. PATENT DOCUMENTS

| | | | | |
|---|---|---|---|---|
| 3,105,916 A | * | 10/1963 | Marker et al. | 313/420 |
| 3,217,135 A | * | 11/1965 | Eklund | 219/121.24 |
| 3,406,304 A | | 10/1968 | Brewster | 313/420 |
| 3,486,060 A | * | 12/1969 | Swanson | 313/420 |
| 3,651,360 A | * | 3/1972 | Sommeria | 313/454 |
| 4,305,000 A | | 12/1981 | Cheever | 250/492.3 |
| 4,721,967 A | | 1/1988 | Roche | 313/420 |
| 4,788,705 A | * | 11/1988 | Anderson | 378/121 |
| 5,175,436 A | | 12/1992 | Puumalainen | 250/493.1 |
| 5,898,261 A | * | 4/1999 | Barker | 313/420 |
| 6,528,799 B1 | * | 3/2003 | Katsap et al. | 250/492.23 |
| 6,685,883 B2 | * | 2/2004 | Schianchi et al. | 422/22 |
| 2002/0014827 A1 | * | 2/2002 | An | 313/446 |
| 2002/0134946 A1 | * | 9/2002 | Kiga et al. | 250/396 R |

FOREIGN PATENT DOCUMENTS

| | | | | |
|---|---|---|---|---|
| FR | 2844916 A | * | 3/2004 | |
| GB | 2153140 A | * | 8/1985 | |

* cited by examiner

ELECTRON GUN WITH A FOCUSING ANODE, FORMING A WINDOW FOR SAID GUN AND APPLICATION THEREOF TO IRRADIATION AND STERILIZATION

TECHNICAL DOMAIN

This invention relates to an electron gun in which the anode is transparent to electrons and forms a window of this gun.

It is particularly applicable to:

polymerisation of products for example such as paints, varnishes and glues, irradiation of surfaces, sterilisation of objects, particularly packaging components such as lids, caps, bottles, preforms, pots, thermoforming films, closing films (films used to close some containers) and for example individual flexible pouches or series of flexible pouches, welding by electron bombardment, food decontamination treatment, and heat treatments, for example such as quenching and amorphisation.

More generally, the invention can be used for all ionisation applications using low energy input in focussed form, ionisation of the type that can be done by laser.

STATE OF PRIOR ART

Refer to the following documents:

[1] CA 1 118 180 A, <<Process and apparatus for cold-cathode electron-beam generation for sterilization of surfaces and similar applications>>, invention from Richard N. Cheever

[2] U.S. Pat. No. 4,721,967 A, <<electron gun printer having window sealing conductive plates>>, invention from Michel Roche.

Document [1] describes a cold cathode electron gun. This gun comprises a conducting window that forms the anode of the gun and through which electrons pass to irradiate the surface of an object or to sterilise this object.

Document [2] describes a printer comprising an electron gun and several windows formed by curved metal plates transparent to electrons.

Therefore, it is known how to make an electron beam in the atmosphere, outside the chamber of the electron gun generating this beam. Since the inside of this chamber is under vacuum, the window through which the electron beam passes must resist atmospheric pressure.

This problem arises particularly when it is required to extract low energy electrons (less than or equal to 500 keV) from the chamber, since the window then has to be very thin. In this case it has to be made curved, for example cylindrical but preferably spherical.

However, another problem arises: for some irradiations by an electron beam, it is useful for the electron beam to be focused.

This is even essential in some cases in which the geometry of the beam is important to suitably irradiate objects, for example milk bottle caps, or to concentrate the energy of the beam at a point so as to reach the very high power densities required for welding, cutting or a surface treatment.

But it is well known that focussing elements in a conventional electron gun, and also deflection elements and electron beam transport elements, are frequently very complex and in all cases are large.

PRESENTATION OF THE INVENTION

The purpose of this invention is to correct the disadvantages mentioned above.

Its purpose is an electron gun, and particularly a gun capable of outputting a low energy electron beam (less than or equal to 500 keV), this beam comprising a curved window transparent to electrons and resistant to atmospheric pressure, that acts both as an anode and a focussing electrode.

The invention makes use of the optical properties of curved surfaces for focussing: it uses the curvature applied to the anode forming a window (so that it resists atmospheric pressure) in cooperation with a cathode that is also curved.

Specifically, the purpose of the invention is an electron gun comprising:

a sealed chamber designed to be under a vacuum (evacuated), a cathode placed inside the chamber and which comprises an emitting face capable of emitting electrons, an anode forming a sealed window, formed facing this emitting face in one of the walls of the chamber, and capable of allowing electrons emitted by this emitting face to pass through, and biasing means to set up a voltage between the anode and the cathode capable of accelerating these electrons towards the anode, the electrons thus accelerated forming a beam that passes through the anode, this electron gun being characterised in that the anode and the emitting face each have a curvature, the curvature of the anode making it capable of resisting a pressure difference between the inside and the outside of the chamber and being designed to cooperate with the curvature of the emitting face to focus the electron beam outside the chamber.

According to one preferred embodiment of the electron gun according to the invention, the voltage set up between the anode and the cathode is capable of applying an energy of less than or equal to 500 keV to the electrons.

Preferably, the emitting face of the cathode comprises an emitting layer capable of emitting electrons when it is heated, the electron gun also comprising means of heating the cathode and therefore this emitting layer.

According to a preferred embodiment of the invention, these heating means comprise a filament capable of emitting electrons when it is heated and bombarding the cathode with these electrons, the cathode and therefore the emitting layer thus being heated by electron bombardment.

According to one particular embodiment of the invention, the anode and the emitting face of the cathode form portions of concentric spheres or portions of coaxial cylinders of revolution.

The anode preferably comprises a thin metallic sheet, for which the thickness may be less than 50 micrometers.

According to one preferred embodiment of the electron gun according to the invention, the biasing means are designed to set up a pulsed voltage between the anode and the cathode in order to accelerate the electrons in pulsed mode.

In this case, according to one particular embodiment corresponding to the case in which the heating means include the filament, the biasing means are provided to raise the cathode to a pulsed negative high voltage with respect to the anode, the anode being connected to the ground, and these biasing means comprise:

auxiliary means capable of outputting a negative pulsed voltage, and a transformer capable of transforming this negative pulsed voltage into the pulsed negative high voltage, this transformer comprising a primary winding connected to the auxiliary means and a secondary winding that comprises three electrical conductors, two of these conductors being provided for heating the filament and to bias this filament with respect to the cathode, so that electrons emitted by the filament reach this cathode, the third conductor being provided to raise the cathode to the pulsed negative high voltage.

The anode is preferably provided with cooling means.

These cooling means preferably comprise means of projecting a gas onto at least part of the periphery of the anode.

This invention also relates to an installation for electronic irradiation of at least one object, this installation comprising means of irradiating this object by a focused electron beam, installation in which the irradiation means comprise the electron gun according to the invention.

This invention also relates to an installation for electronic sterilisation of objects, particularly packaging components, this installation comprising means of irradiating these objects by a focused electron beam, installation in which the irradiation means comprise the electron gun according to the invention.

BRIEF DESCRIPTION OF THE DRAWING

This invention will be better understood after reading the following example embodiments given below, purely for guidance and in no way limitative, with reference to the attached drawings on which.

DETAILED PRESENTATION OF PARTICULAR EMBODIMENTS

Figure 1:
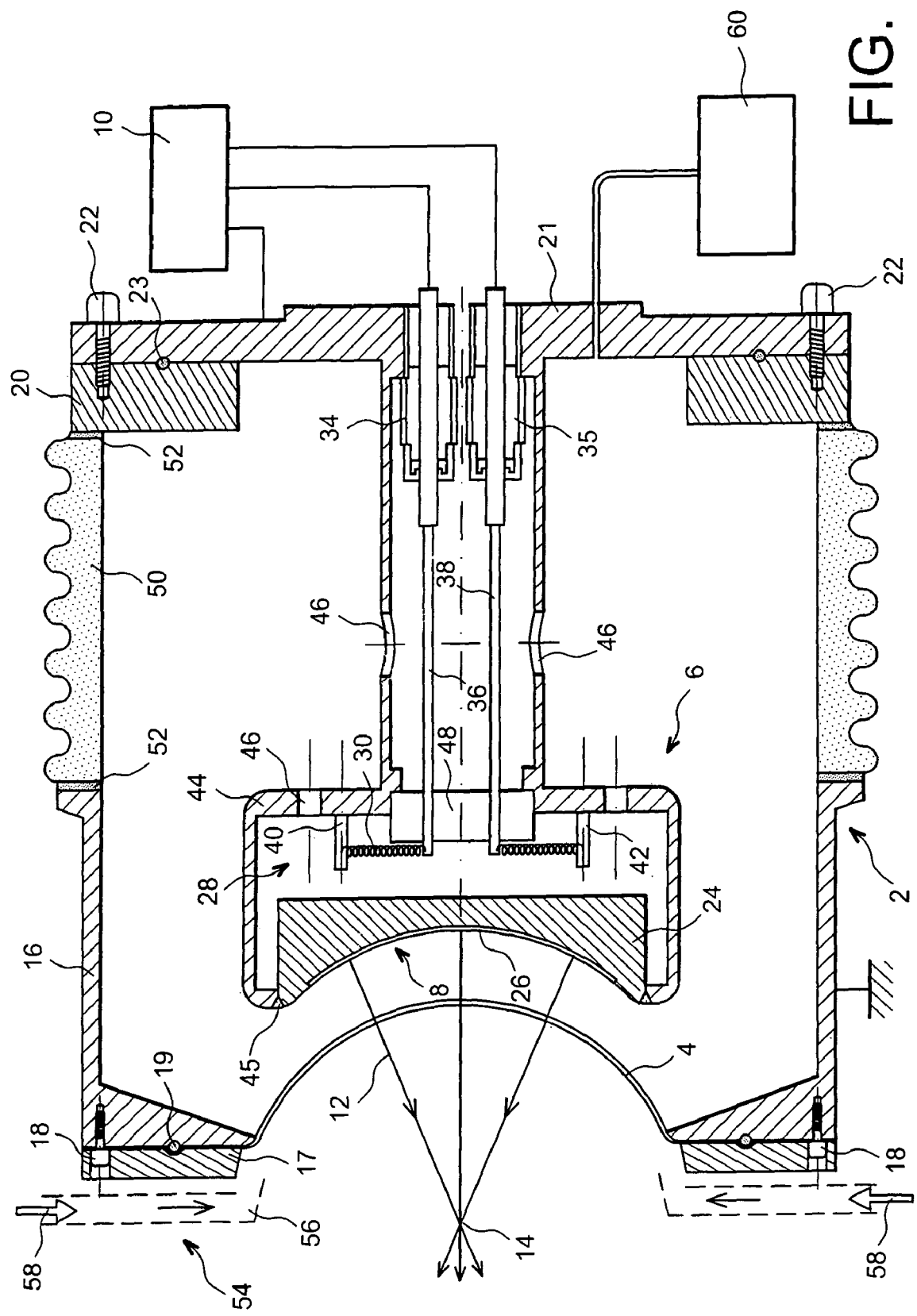
FIG. 1 is a longitudinal diagrammatic sectional view of a particular embodiment of the electron gun according to the invention.

The electron gun according to the invention that is diagrammatically shown in section in FIG. 1, comprises a sealed chamber 2 that is under a vacuum, and an anode 4 and a cathode 6. The cathode 6 is placed in the chamber 2 and comprises an emitting face 8 capable of emitting electrons.

The anode 4 is formed in one of the walls of the chamber facing this emitting face 8, and forms a sealed window transparent to electrons. Thus, electrons that are emitted by the emitting face can pass through it.

The electron gun also comprises electrical power supply means 10 capable of setting up an acceleration voltage Va between the anode 4 and the cathode 6, to accelerate electrons emitted by the cathode towards the anode. In the example shown in FIG. 1, the anode 4 is connected to the ground and the voltage Va is a pulsed negative high voltage applied to the cathode.

Electrons thus accelerated form a beam 12 that passes through the anode 4 and is outside the chamber 2, in other words in air.

According to the invention, the anode 4 and the emitting face 8 are each curved. The curvature of the anode enables it to resist the pressure difference between the inside of the chamber that is under a vacuum, and the outside of this chamber that is at atmospheric pressure. Furthermore, the curvature of the anode cooperates with the curvature of the emitting face to focus the electron beam 12 outside the chamber.

In the example in FIG. 1, the focusing zone 14 that will be discussed further later, is a point or a straight line.

The chamber 2 maintains the seal under a vacuum more precisely the secondary vacuum in the example, and comprises a first approximately cylindrical metallic part 16, for example made of stainless steel, connected to the ground and that supports the anode 4, and a second approximately annular metallic part 20 connected to the cathode 6 and therefore to the pulsed negative high voltage Va.

In the example shown, the anode 4 is made from a metallic sheet that will be discussed in more detail later. The edge of this sheet is fixed in place between the metallic part 16 and an approximately annular part 17.

This part 17 is clamped in contact with the metallic part 16 by screws 18. On the side of this part 16 and the part 17, the chamber is sealed using a metallic seal 19, for example made of indium, that is clamped with the metallic sheet, between the metallic sheet and the metallic part 16 as can be seen in FIG. 1.

The metallic part 20 is closed by a flange 21 that forms the backwall of the chamber 2. It is opposite the wall supporting the anode 4 namely the front wall. Screws 22 are used to clamp the flange 21 in contact with the metallic part 20.

On the side of this part 20, the chamber is sealed by means of another metallic seal 23, for example made of indium, that is clamped between the metallic part 20 and the flange 21 as can be seen in FIG. 1.

The gun in FIG. 1 is designed to output a pulsed low energy electron beam, not exceeding 500 keV. For example, a 250 keV beam with a power of 5 kW may be produced, but this is in no way limitative.

The cathode 6 comprises a metallic part 24, for example made of nickel, for which the face towards the anode forms the face 8 that emits electrons. To achieve this, a thin layer 26 a few tens of millimetres thick is deposited on this face 8, that emits electrons when it is heated and that may for example consist of a mix of nickel powder and sintered barium carbonate.

For example, 5% to 10% by volume of $BaCO_3$ could be used sintered to 1000° C. under a hydrogen atmosphere, but this is in now way limitative.

Means 28 are provided to heat the part 24 and therefore the layer 26. In the example, this consists of heating means by electron bombardment comprising a filament 30, for example made of tungsten, that emits electrons when it is heated.

Two sealed crossings 34 and 35 of the ceramic-metal type are welded on the flange 21 and are used for the electrical power supply of the filament 30 through metallic rods 36 and 38 respectively, as can be seen in FIG. 1.

The filament 30 facing the part 24 is supported by ceramic screws such as screws 40 and 42, to electrically isolate the filament from the cathode. Obviously, this filament is continuous but only its two ends can be seen in FIG. 1, the remainder remaining "behind" the plane of the figure.

As can be seen, the cathode comprises another part 44 made of stainless steel, provided with vent holes 46 and fixed firstly to the part 24, for example by a spot weld 45 such as a TIG weld, and at the other end to the flange 21.

The part 44 is fitted with ceramic screws such as screws 40 and 42 and is hollow; rods 36 and 38 pass through it and are electrically insulated from it by a ceramic ring 48, as can be seen in FIG. 1.

The electrical insulation of the filament 30 from the cathode 6 and therefore from the nickel part 24 makes it possible to apply an appropriate bias voltage between this part and the filament, to bombard the part 24 with electrons emitted by the filament, and therefore to heat the part.

In the example, the filament is negatively biased to −500 V with respect to the cathode.

The chamber 2 comprises a third part 50, more or less in the form of a sleeve, that forms an electrical insulator resisting high voltage and that holds parts 16 and 20 of the chamber fixed to each other. It is preferable to use a ceramic insulator, for example made of alumina.

Ceramic-metal type brazings 52 at the two ends of this insulator seal the connection between the insulator 50 and the metal parts 16 and 20.

In the example, the anode 4 and the face 8 of the part 24 may form portions of concentric spheres in which case the focusing zone 14 of the electron beam 12 is a point, or they may form portions of coaxial cylinders of revolution in which case this zone is a straight-line (parallel to the common axis of the cylinders, this axis then being perpendicular to the plane of FIG. 1).

As can be seen in FIG. 1, the electron emitting layer 26 stops slightly before the edge of the part 24 so as to only accelerate the electron beam 12 in a zone in which the electric field generated in the accelerator space (in other words the space between the anode and the cathode) by application of the voltage Va, is not affected by edge effects.

The electron beam 12 is focused essentially by the convergence of electrical field lines in this accelerator space in which preferably the field hardly exceeds 160 kV/cm. For guidance, and in no way limitatively, a 250 keV beam is created by providing a distance of 1.5 cm between the anode 4 and the cathode 6, resulting in an electric field that satisfies the above condition.

The anode 4 is composed of a thin metallic sheet, preferably made of titanium or aluminium. The thickness of this sheet must be lower as the energy required for the electron beam is lower.

For a beam not exceeding 500 keV, it is preferable to use a sheet with a thickness of less than 50 micrometers.

For example, the electron gun in FIG. 1 may use a spherical shaped titanium sheet with a radius of curvature equal to 35 mm, and with a thickness advantageously between 10 µm and 15 µm.

Anode 4, that forms the window of the gun in FIG. 1, is provided with means 54 of splashing air on at least part of the periphery of this window, for example on half or possibly all of this periphery, so as to cool the window.

As can be seen, these means 54 comprise a compressed air inlet 56 on the required peripheral part, this inlet 56 being supplied with compressed air by means symbolised by the arrows 58.

It is preferable to very thoroughly filter air directed to the periphery of the anode to prevent it from containing any dust.

This dust could stick to the anode where it would be heated by the electron beam and could then cause penetration of the anode.

The electron gun in FIG. 1 may also be fitted with suction means (not shown) for cooling the anode with a practically controlled atmosphere (for example a nitrogen atmosphere) to prevent the formation of ozone (dangerous gas) during operation of the electron gun.

Furthermore, before the gun in FIG. 1 is made to operate, a vacuum is created in the chamber 2: a secondary vacuum is created in it, in other words a pressure less than or equal to $10^{-5}$ Pa.

This vacuum can be maintained <<statically>> in the chamber, provided that only <<ultra-vacuum>> techniques are used and provided that prolonged degassing is done at high temperature, for example 300° C., when creating the secondary vacuum in the chamber, and provided that a getter (not shown) is then used in the chamber to maintain the secondary vacuum thus obtained in the chamber.

As a variant, this secondary vacuum could be created in the chamber 2 and could then be maintained <<dynamically>>, for example using an ion pump 60.

For example, the electron gun in FIG. 1 may be in the form of an approximately 400 mm long and 50 mm diameter cylinder, but this is in no way limitative.

One preferred embodiment of the electron gun according to the invention is based on two principles, namely acceleration in pulsed mode and acceleration in <<diode>> mode. The electron gun in FIG. 1 is an example of this preferred embodiment.

Concerning acceleration in pulsed mode, instead of applying a permanent electron acceleration voltage to a gun outputting a low electron current, for example 10 mA, the electron acceleration voltage is applied only during a small fraction of the time during which the gun is used, preferably 1 thousandth of this time. For example, this voltage is applied for 2 us at a repetition rate of 500 Hz, but obviously the current must be 1000 times higher and therefore equal to 10 A.

This has the advantage that it reduces electrical insulation constraints that are much less severe for a short pulse (the probability of a breakdown varying with the square root of the voltage application time). The result is a reduction in the size and costs of high voltage generators and the electron gun.

Furthermore, the compactness of this gun has many complementary advantages, particularly the reduction of shielding volumes.

Figure 2:
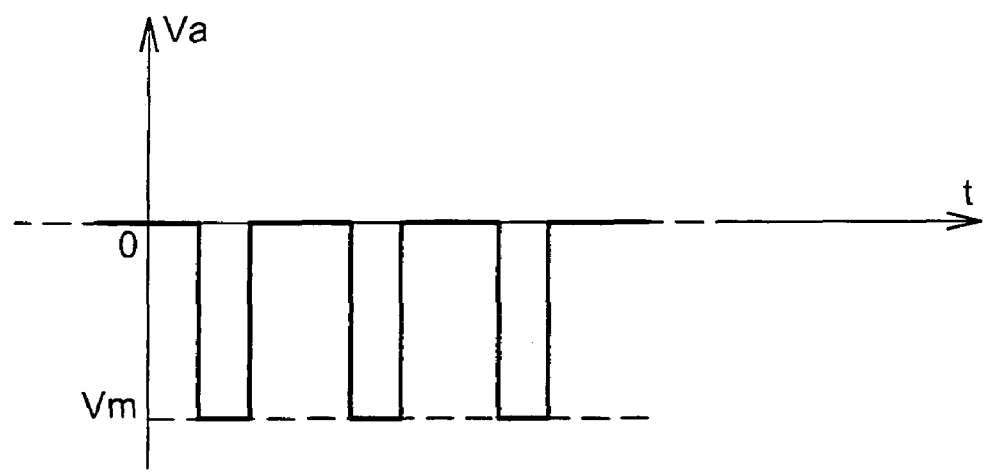
FIG. 2 shows variations as a function of time t, of a pulsed high voltage Va that can be applied to the cathode of the electron gun in FIG. 1 to accelerate electrons emitted by this cathode, FIG. 3 diagrammatically shows acceleration in diode mode possible with this electron gun in FIG. 1.

FIG. 2 shows variations with time t of a pulsed negative high voltage Va that can be applied to the cathode of an electron gun according to the invention, for example the gun in FIG. 1, to accelerate electrons emitted by this cathode.

The minimum (negative) value of this voltage Va is denoted Vm. Therefore, Vm is the value of the voltage periodically applied to the cathode, for only a fraction of the gun usage time.

Figure 3:
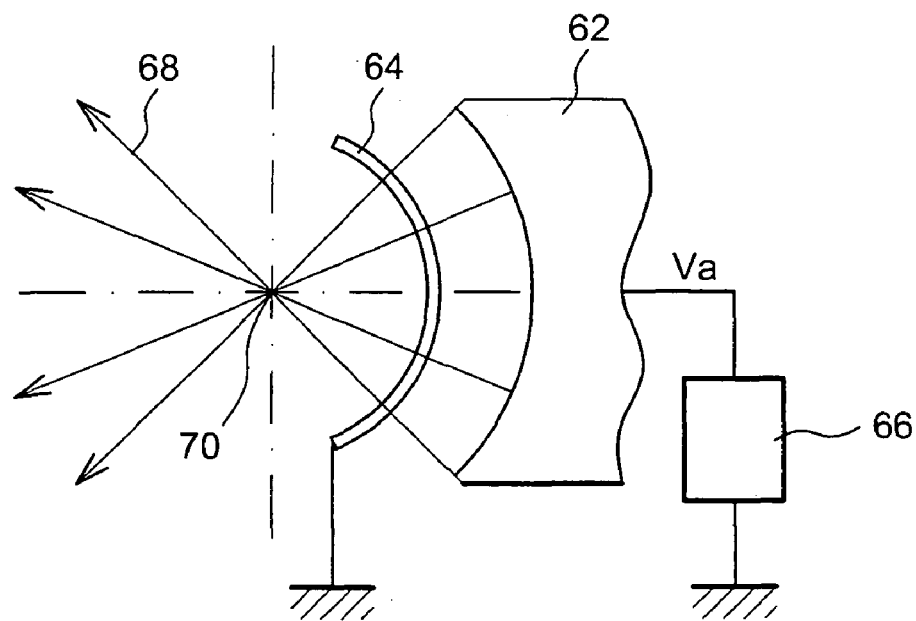

Acceleration in <<diode>> mode is the simplest possible method of accelerating electrons: the electrons are accelerated between a hot cathode 62 and an anode 64 that are diagrammatically shown in FIG. 3 (and correspond to the cathode 6 and the anode 4 respectively in the example shown in FIG. 1).

Means 66 are also shown for applying the voltage Va to the cathode 62, the anode 64 being connected to the ground.

The simplicity of the electron gun obtained becomes obvious considering that with this acceleration mode, the anode also acts as a necessary window for the exit of electrons into the atmosphere, with a well controlled beam width adapted to most usage cases.

The electron beam focusing, deflection and transport elements used in a conventional electron accelerator are all eliminated, and these elements are often very complex and in any case are large.

As has already been mentioned, the anode has a curvature (in the concave sense for an observer on the atmosphere side) that is necessary to resist the atmospheric pressure despite the thinness of this anode and that is also used to focus the electron beam 68 (FIG. 3) directly in the accelerator space such that the focusing area 70 is outside the electron gun.

Figure 4:
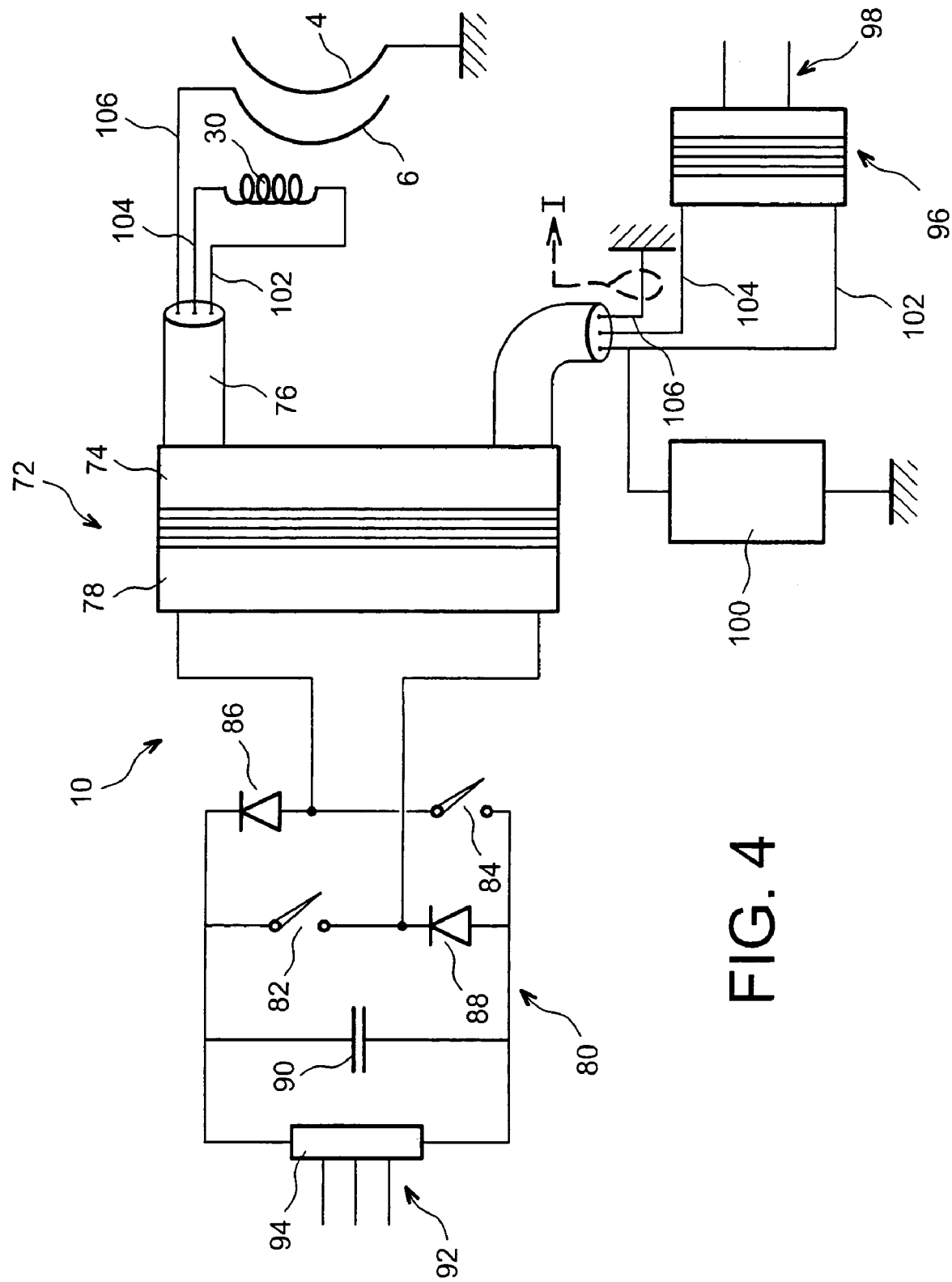
FIG. 4 shows a diagram of electrical power supply means of the electron gun in FIG. 1, FIG. 5 diagrammatically shows an application of an electron gun according to the invention, to sterilisation of a wrapping film, FIG. 6 diagrammatically shows an application of an electron gun according to the invention, to sterilisation of packaging components such as caps or lids, and FIGS. 7 and 8 diagrammatically illustrate other applications of the invention for the treatment of objects for which shapes can be complex.

FIG. 4 diagrammatically shows an example of electrical power supply means 10 for the electron beam in FIG. 1.

These means 10 are capable of applying the negative pulsed high voltage Va to the cathode 6, biasing the filament 30 with respect to this cathode and heating this filament, the anode 4 being connected to the ground.

These means 10 comprise a transformer 72 used to obtain the negative pulsed high voltage. This transformer 72 is characterised essentially by a very good electrical insulation that can advantageously be made by oil, and by a low leakage inductance.

This low leakage inductance is necessary to obtain sufficiently steep rising fronts for the output pulse, the duration of these rising fronts for example being equal to 1 microsecond, so that time during which the actual high voltage is applied on the electron gun can be minimized, for example to a few microseconds.

The secondary winding 74 of this transformer 72 is wound using a cable 76 with three electrical conductors so that the high voltage can be applied to the cathode, but also from the ground potential, to heat the filament 30 and apply a negative voltage Vf between this filament and the cathode 6 to apply a negative bias to the filament with respect to the cathode, to heat the cathode by electron bombardment, to a high temperature for example of the order of 800° C.

The voltage Vf thus controls the temperature of the cathode 6. This temperature itself controls the emissivity of the cathode.

It should be noted that all these controls, namely controls for application of the pulsed high voltage to the cathode, for heating the filament, and for applying the bias voltage to the filament with respect to the cathode, are made very simply from the ground potential despite the presence of very high voltage pulses.

The transformer 72 is controlled through an asymmetrical bridge 80 that is connected to the primary winding 78 of this transformer and is designed to supply a pulsed negative voltage to it that the transformer converts into a pulsed negative high voltage.

This asymmetric bridge 80 comprises two switching transistors 82 and 84 and two diodes 86 and 88, these diodes and transistors being arranged as can be seen in FIG. 4. The two diodes 86 and 88 make it possible to demagnetise the transformer 72. The two transistors 82 and 84 are preferably IGBT transistors, in other words insulated gate bipolar transistors.

Furthermore, the transistors 82 and 84 are controlled by means not shown for obtaining the pulse rate required for the voltage.

For example, these means may be optocoupled <<driver>> type integrated circuits.

The asymmetric bridge 80 is powered by capacitor 90 under a power supply voltage obtained by rectification of the three-phase mains power supply 92 using a Graetz bridge diagrammatically shown by the rectangle 94.

For example, the asymmetric bridge 80 is powered by a capacitor with a capacitance of a few hundred microfarads at a voltage of the order of 500 V obtained by rectification of the three-phase mains power supply using the Graetz bridge.

The power supply means 10 also comprise another transformer 96 for which the primary winding is connected to the single phase mains power supply 98 (220 V-50 Hz). This transformer 96 makes it possible to heat the filament 30 by means of an alternating current with a frequency that may for example be equal to 50 Hz and with an intensity of 5 A, and under a voltage equal to for example 6V.

The electrical power supply means 10 also comprise a generator 100 designed to output a direct voltage that controls the temperature of the cathode 6. This DC voltage may for example be variable between 100 V and 500 V.

The cathode 6 is preferably used in saturated mode. In this case, the density of the current that can be extracted from the accelerator space (space between the cathode and the anode) only depends on the temperature of this cathode. Thus, the current output by the electron gun is solely controlled by means of this DC voltage.

This voltage may possibly be controlled by a slaving loop (not shown) from reading the current I output in a negative high voltage pulse output to the cathode.

We will now give a more detailed description of the secondary winding of the transformer 72. The cable 76 from which this winding is formed includes three conductors 102, 104 and 106 that are electrically insulated from each other.

The conductors 102 and 104 connect the two terminals of the filament 30 to the corresponding two terminals of the secondary winding of the transformer 96. Furthermore, the generator 100 is installed between the ground and the end of the conductor 102 located on the side of the transformer 96. The ends of the conductor 106 are also connected to the cathode 6 and to the ground respectively.

Although operation in pulsed mode is a preferred embodiment of the invention, the invention is not limited to this operation; the cathode can be biased with respect to the anode of an electron gun according to the invention by means of a DC voltage, to obtain operation in continuous mode.

Similarly, although the use of a hot cathode corresponds to a preferred embodiment of the invention, the invention is not limited to such a use: other types of cathodes can be used in an electron gun according to the invention, for example a cold cathode capable of emitting electrons by a field effect.

Furthermore, the invention is not limited to the supply of an electron beam not exceeding 500 keV: higher energies are possible with the invention, by adapting the bias of the cathode with respect to the anode of an electron gun according to the invention.

Furthermore, although the invention is designed to supply an electron beam in air, it is obvious that an electron gun according to the invention could be used to output such a beam in a vacuum.

Various applications of the electron gun according to the invention have already been mentioned above. The electron gun is particularly adapted to these applications because it can be manufactured to be compact and inexpensive, and it can be used to create a low energy electron beam with a high penetration capacity.

Figure 5:
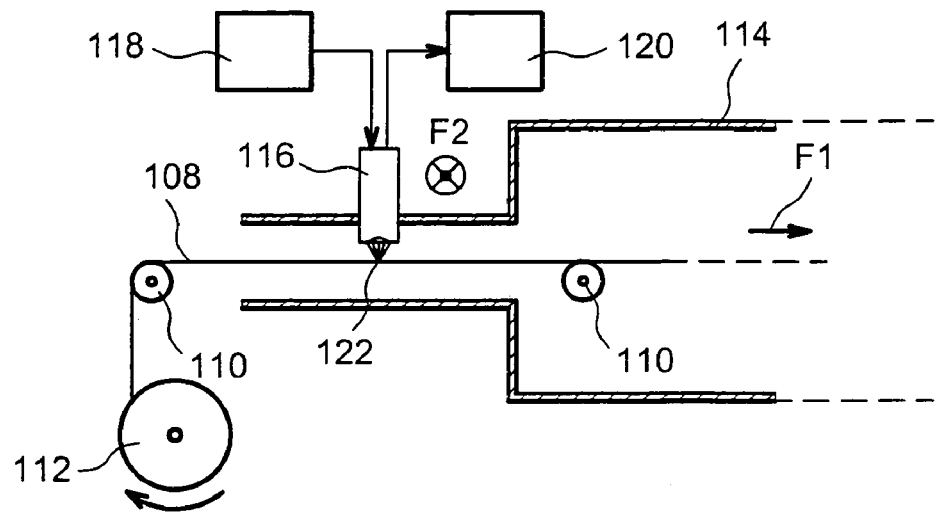
Figure 6:
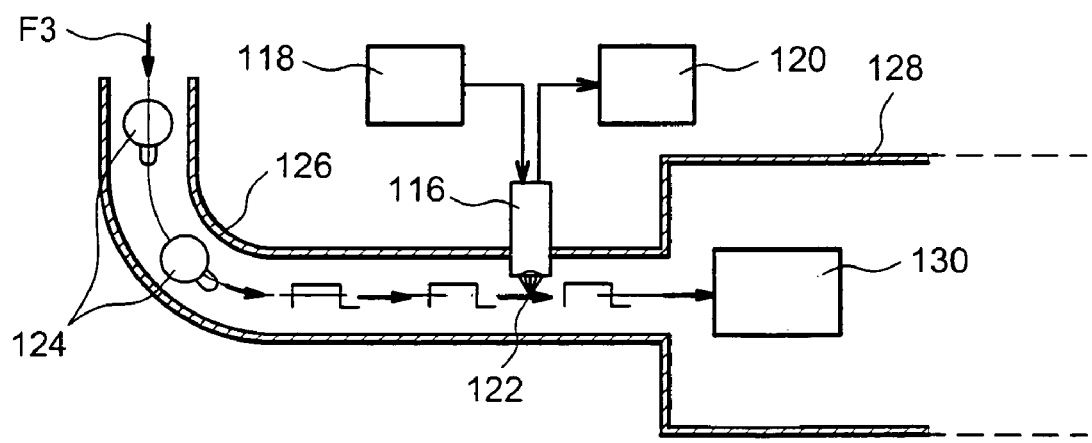

The following contains two example applications of the invention with reference to FIGS. 5 and 6.

FIG. 5 diagrammatically shows an application of the invention to sterilisation of a wrapping film 108, for example a thermoforming film or a closing film.

This film 108 is tensioned and is displaced (along the direction of the arrow F1, from left to right on the figure) on rollers 110, by means not shown, starting from a coil 112 onto which it is wound. As can be seen on the Figure, after the film 108 has been unwound from the coil, it penetrates and moves into the aseptic chamber 114 that is pressurised by means not shown.

An electron gun 116 according to the invention provided with pumping means 118 and biasing means 120 is provided at the entry to the aseptic chamber 114 to sterilise the film 108 by an electron beam 122 output by the gun 116 before the film penetrates into the chamber.

The gun is arranged so as to focus the beam on the film 108. Means symbolically shown by arrows F2 are provided to apply forward/return movements to the gun along the width of the film 108, such that the focussed beam scans the film along its width and therefore scans the entire film due to the displacement of the film along the direction of the arrow F1, that is perpendicular to the arrows F2.

An electron gun with cylindrical focusing could also be used to avoid the need to displace it. In this case, the focal point is a line with a length longer than the width of the film being treated.

FIG. 6 diagrammatically shows another application of the invention to sterilisation of packaging components 124, for example such as caps or lids.

These components 124 are pushed by a sterile air jet (diagrammatically shown by arrow F3) and starting from means not shown, in a vertical duct 126 in which the components drop by gravity. This duct 126 is connected to an aseptic chamber 128 that is pressurised by means not shown.

When they arrive in this chamber, the components 124 are gripped by mechanical means shown symbolically by the rectangle 130, and are carried by these means to other means not shown, designed for use of components in the chamber.

An electron gun 116 according to the invention is then provided in front of the chamber 128 to sterilise components 124 before they enter into this chamber, using the focused electron beam 122 output by this gun.

Several electron guns according to the invention could be coupled together to treat the surface of possibly complex-shaped objects, with no penetration. This is diagrammatically shown in FIGS. 7 and 8.

Figure 7:
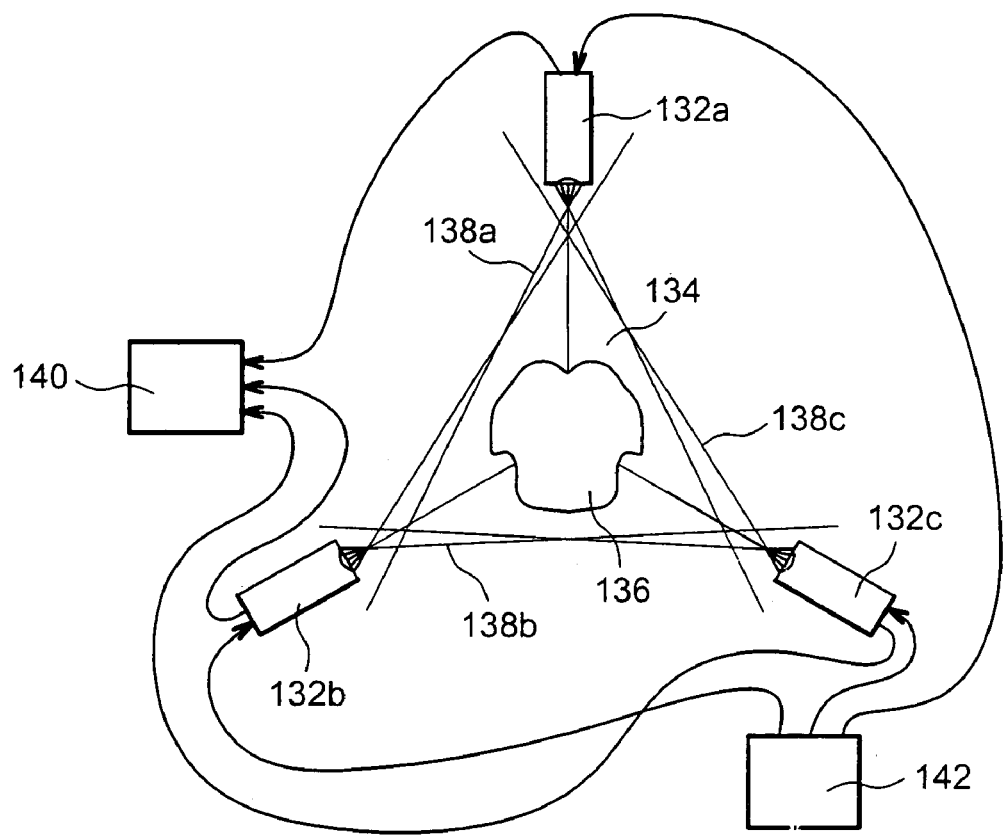

FIG. 7 shows three electron guns according to the invention, 132a, 132b and 132c, that are located at 120° from each other. The intersection of the electron beams that are emitted by these guns covers an area 134 in which an object 136 with a complex shape is placed, for which the surface is to be treated by electronic irradiation.

As can be seen in FIG. 7, each of the electron guns 132a, 132b or 132c emits a beam 138a, 138b or 138c for which the divergence from the corresponding focal area is not excessive, so as to not irradiate the other two guns.

The electron guns 132a, 132b and 132c are provided with pumping means 140. They are also provided with control means 142 allowing the guns to simultaneously emit pulsed electron beams.

Figure 8:
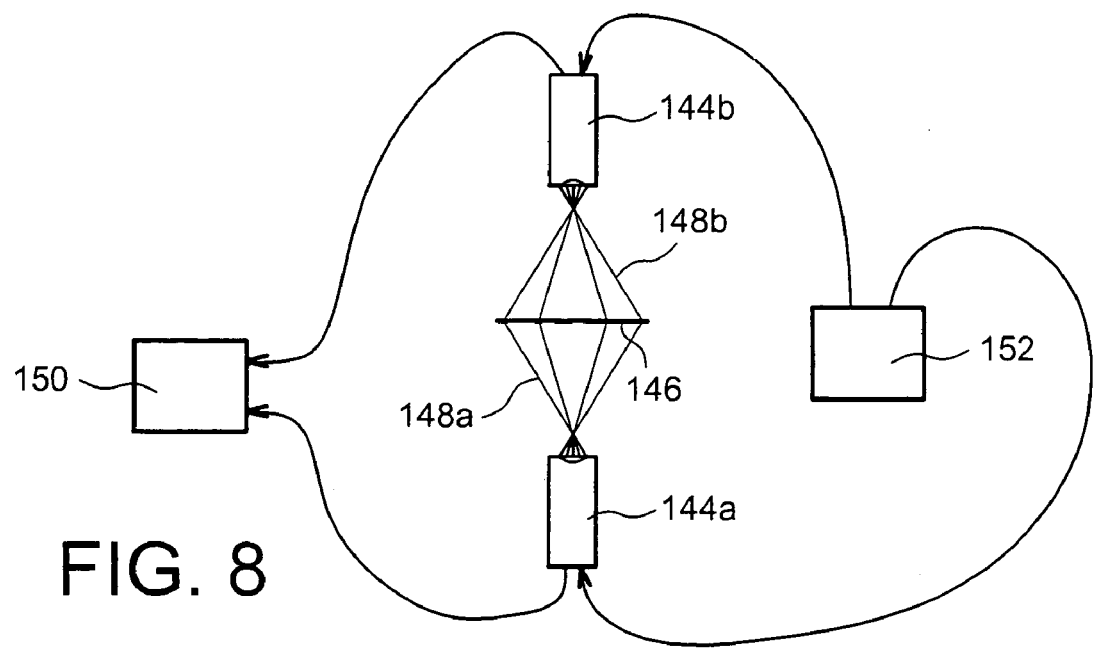

FIG. 8 shows two electron guns 144a and 144b according to the invention, placed facing each other, so that an area between these two guns can be irradiated. An object 146 is placed in this area, approximately equidistant from the two guns, so as to be able to treat the two sides of the object by two electron beams 148a and 148b emitted by the guns.

The electron guns 144a and 144b are provided with pumping means 150. They are also provided with the control means 152 that the guns can use to simultaneously emit pulsed electron beams.

These means 152 are activated only when the object 146 is inserted between the two guns, so that one of the guns is not damaged by the beam emitted by the other gun, and vice versa.

The invention claimed is:

1. Electron gun comprising:
    a sealed chamber, designed to be under a vacuum,
    a cathode placed inside the chamber and which comprises an emitting face, capable of emitting electrons,
    an anode forming a sealed window, formed facing this emitting face in one of the walls of the chamber, and capable of allowing electrons emitted by this emitting face to pass through, and
    biasing means to set up a voltage between the anode and the cathode, capable of accelerating these electrons towards the anode, the electrons thus accelerated forming a beam that passes through the anode,
    this electron gun being characterised in that the anode and the emitting face each have a curvature, the curvature of the anode making it capable of resisting a pressure difference between the inside and the outside of the chamber and the curvature of the anode being designed to cooperate with the curvature of the emitting face to focus the electron beam outside the chamber.

2. Electron gun according to claim 1, in which the voltage set up between the anode and the cathode is capable of applying an energy of less than or equal to 500 keV to the electrons.

3. Electron gun according to claim 1, in which the emitting face of the cathode comprises an emitting layer, capable of emitting electrons when it is heated, the electron gun also comprising means for heating the cathode and therefore the emitting layer.

4. Electron gun according to claim 3, in which these heating means comprise a filament capable of emitting electrons when it is heated and bombarding the cathode with these electrons, the cathode and therefore the emitting layer thus being heated by electron bombardment.

5. Electron gun according to claim 4, in which the biasing means are designed to set up a pulsed voltage between the anode and the cathode, in order to accelerate the electrons in pulsed mode and in which the biasing means are designed to raise the cathode to a pulsed negative high voltage with respect to the anode, the anode being connected to the ground, and these biasing means comprise:
    auxiliary means capable of outputting a negative pulsed voltage, and
    a transformer capable of transforming this negative pulsed voltage into the pulsed negative high voltage,
    this transformer comprising a primary winding connected to the auxiliary means and a secondary winding that comprises three electrical conductors, two of these conductors being provided for heating the filament and to bias this filament with respect to the cathode, so that electrons emitted by the filament reach this cathode, the third conductor being provided to raise the cathode to the pulsed negative high voltage.

6. Electron gun according to claim 1, in which the anode comprises a thin metallic sheet, for which the thickness is less than 50 micrometers.

7. Electron gun according to claim 1, in which the biasing means are designed to set up a pulsed voltage between the anode and the cathode, in order to accelerate the electrons in pulsed mode.

8. Electron gun according to claim 1, in which the anode and the emitting face of the cathode form portions of concentric spheres or portions of coaxial cylinders of revolution.

9. Electron gun according to claim 1, in which the anode is provided with cooling means.

10. Electron gun according to claim 9, in which these cooling means comprise means of projecting a gas onto at least part of the periphery of the anode.

11. Installation for electronic irradiation of at least one object, this installation comprising means of irradiating this object by a focused electron beam, installation in which the irradiation means comprise the electron gun according to claim 1.

12. Installation for electronic sterilisation of objects, this installation comprising means of irradiating these objects by a focused electron beam, installation in which the irradiation means comprise the electron gun according to claim 1.

13. Installation for electronic sterilisation of packaging components, this installation comprising means of irradiating these packaging components by a focused electron beam, installation in which the irradiation means comprise the electron gun according to claim 1.

* * * * *

UNITED STATES PATENT AND TRADEMARK OFFICE
CERTIFICATE OF CORRECTION

PATENT NO.       : 7,800,012 B2
APPLICATION NO.  : 10/576034
DATED            : September 21, 2010
INVENTOR(S)      : Michel Roche and Philippe Fontcuberta Page 1 of 1

It is certified that error appears in the above-identified patent and that said Letters Patent is hereby corrected as shown below:

In Column 6, line 37 please delete "us" and insert therefor --µs--.

Signed and Sealed this
Fourth Day of January, 2011

David J. Kappos
*Director of the United States Patent and Trademark Office*